US010898863B2

(12) United States Patent
Hiraoka et al.

(10) Patent No.: US 10,898,863 B2
(45) Date of Patent: Jan. 26, 2021

(54) HOLLOW-FIBER MEMBRANE AND HOLLOW-FIBER MODULE FOR CELL CULTURE

(71) Applicant: TOYOBO CO., LTD., Osaka (JP)

(72) Inventors: Makiko Hiraoka, Otsu (JP); Tatsuya Yamaguchi, Otsu (JP); Noriaki Kato, Otsu (JP)

(73) Assignee: TOYOBO CO., LTD., Osaka (JP)

( * ) Notice: Subject to any disclaimer, the term of this patent is extended or adjusted under 35 U.S.C. 154(b) by 303 days.

(21) Appl. No.: 15/781,859

(22) PCT Filed: Dec. 9, 2016

(86) PCT No.: PCT/JP2016/086685
§ 371 (c)(1),
(2) Date: Jun. 6, 2018

(87) PCT Pub. No.: WO2017/104557
PCT Pub. Date: Jun. 22, 2017

(65) Prior Publication Data
US 2018/0361325 A1 Dec. 20, 2018

(30) Foreign Application Priority Data
Dec. 15, 2015 (JP) .................................. 2015-244000

(51) Int. Cl.
| B01D 69/02 | (2006.01) |
| B01D 63/04 | (2006.01) |
| B01D 69/08 | (2006.01) |
| B01D 71/68 | (2006.01) |
| C12M 1/12 | (2006.01) |
| B01D 71/44 | (2006.01) |

(52) U.S. Cl.
CPC .............. *B01D 69/02* (2013.01); *B01D 63/04* (2013.01); *B01D 69/08* (2013.01); *B01D 71/44* (2013.01); *B01D 71/68* (2013.01); *C12M 25/10* (2013.01); *C12M 25/12* (2013.01); *B01D 2325/36* (2013.01); *B01D 2325/38* (2013.01)

(58) Field of Classification Search
CPC .................................................... B01D 69/02
See application file for complete search history.

(56) References Cited

U.S. PATENT DOCUMENTS

2011/0210067 A1* 9/2011 Kato ................... B01D 61/147
210/634

FOREIGN PATENT DOCUMENTS

| EP | 2335814 A1 | 6/2011 |
| EP | 2412798 A1 | 2/2012 |
| JP | 62-130678 A | 6/1987 |
| JP | 4-117600 U | 10/1992 |
| JP | 10-180058 A | 7/1998 |
| JP | 2000-254222 A | 9/2000 |
| JP | 2009-540865 A | 11/2009 |
| JP | 2010-523118 A | 7/2010 |
| JP | 2011-56458 A | 3/2011 |
| JP | 2012-503688 A | 2/2012 |
| JP | 2014-60991 A | 4/2014 |
| JP | 2014-79687 A | 5/2014 |
| JP | 2014-117190 A | 6/2014 |
| WO | 2008/002914 A2 | 1/2008 |
| WO | 2008/124229 A2 | 10/2008 |
| WO | 2010/034466 A1 | 4/2010 |
| WO | 2010/035793 A1 | 4/2010 |

OTHER PUBLICATIONS

Extended (Supplementary) European Search Report dated Jun. 25, 2019, issued in counterpart EP application No. 16875537.9. (8 pages).
Zhou Yuan et al., "Porous PVDF/TPU blends asymmetric hollow fiber membranes prepared with the use of hydrophilic additive PVP (K30)", Science Direct Desalination, vol. 223, No. 1-3, Mar. 1, 2008, pp. 438-447, cited in Extended (Supplementary) European Search Report dated Jun. 25, 2019. (10 pages).
International Search Report dated Feb. 21, 2017, issued in counterpart application No. PCT/JP2016/086685. (2 pages).

\* cited by examiner

*Primary Examiner* — Scott Long
(74) *Attorney, Agent, or Firm* — Westerman, Hattori, Daniels & Adrian, LLP (57) ABSTRACT

An object of the present invention is to provide a hollow-fiber membrane which does not require a coating treatment with a cell adhesion factor or surface modification by an electron beam or the like and which is capable of adhering and culturing cells, and a method for culturing cells using the hollow-fiber membrane. A hollow-fiber membrane for cell culture which is to be used as a culture substrate for adhesive cells, in which the hollow-fiber membrane includes a hydrophobic polymer and a hydrophilic polymer, the content of the hydrophilic polymer in the whole hollow-fiber membrane is more than 0% by mass and less than 1% by mass, and the content of the hydrophilic polymer on a surface of the hollow-fiber membrane is more than 0% by mass and less than 10% by mass.

7 Claims, 2 Drawing Sheets

HOLLOW-FIBER MEMBRANE AND HOLLOW-FIBER MODULE FOR CELL CULTURE

TECHNICAL FIELD

The present invention relates to a hollow-fiber membrane to be used as a culture substrate for culturing cells.

BACKGROUND ART

Stem cells are cells that can form organs and tissues, and are considered to exist present in most organs and tissues even in adults. Among stem cells, embryonic stem cells (ES cells) and induced pluripotent stem cells (iPS cells) are pluripotent cells, and are capable of being differentiating into all tissues and organs. On the other hand, somatic stem cells cannot differentiate into all organs and tissues, and differentiate into specific tissues and organs. Somatic stem cells collectable from human tissues are attracting attention as transplanting cells to be used in cell transplantation therapy because they can be collected from patients themselves, and there is no fear of rejection.

As somatic stem cells in humans, mesenchymal stem cells, hematopoietic stem cells, neural stem cells, myocardial stem cells, pancreatic stem cells, skin stem cells, bone marrow stem cells, retinal stem cells, corneal endothelial stem cells and the like have been heretofore known. However, there exist an extremely small number of such somatic stem cells in tissues.

Thus, studies have been advanced on a cell transplantation therapy in which somatic stem cells obtained from living tissues are cultured outside a living body, amplified to a cell number necessary for therapy, and then used for treatment of the same person or other persons, and the cell transplantation therapy has started being put into practical use.

However, in cell culture operations that are generally carried out, there is the problem that the risk of biological contamination is high, and costs associated with personnel expenses are high, and therefore it is required to safely and inexpensively culture stem cells for further development of cell transplantation therapy.

Incidentally, cells adhesive in a living body cannot grow or survive outside the living body unless the cells adhere to a culture substrate. Thus, culturing of adhesive stem cells requires a cell adhesion factor such as collagen or fibronectin which promotes adhesion of the cells to the culture substrate.

PTD 1 discloses a cell culture system using a hollow-fiber membrane. In this literature, two kinds of hollow-fiber membranes are shown as bases for seeding cells, and DESMOPAN (registered trademark) (0.5% thermoplastic polyurethane) and POLYFLUX (trade name) (polyamide+polyaryl ether sulfone+polyvinyl pyrrolidone mixture) are tested. While properties of these membranes are unknown, POLYFLUX is a hydrophilized film because it is made of a mixture of polyvinyl pyrrolidone. In addition, PTD 2 discloses a cell culture system including a hollow-fiber membrane containing 65 to 95% of a hydrophobic polymer and 5 to 35% of a hydrophilic polymer, and an example of using POLYFLUX described above. These literatures suggest that efficient extended culture can be performed by a hollow-fiber membrane-type cell culture apparatus. However, these literatures suggest that by performing a surface treatment with platelet lysates, plasma, fibronectin or the like prior to use of a membrane in culture of cells, desired culture can be performed, and it is necessary to coat a base with some cell adhesion factor beforehand in culture of adhesive cells. PTD 3 discloses a technique using a hollow-fiber membrane in culture of floating cells. This literature suggests that a gas is supplied, and a medium is exchanged while a hydrophobic hollow-fiber membrane is used, but here, the hollow-fiber membrane is not used as a base for cell culture. In addition, PTD 4 discloses a technique in which a membrane containing polysulfone, polyether sulfone or polyaryl ether sulfone as a hydrophobic polymer, and polyvinyl pyrrolidone as a hydrophilic polymer is irradiated with 12.5 to 175 kGy of a gamma ray, beta ray or electron beam in the presence of oxygen with a concentration of 4 to 100 vol % to modify a surface, so that adhesive cells can be cultured without performing some pretreatment.

However, when a culture substrate is coated with such a cell adhesion factor, material costs of the adhesion factor and operation costs are increased. In addition to the problem of cost increase, there arises the additional risk of unknown infection when the cell adhesion factor is an animal-derived component. In recent years, the risk of infection has been reduced by using a cell adhesion factor produced by gene-recombinant *Escherichia coli*, but in this production, complicated operations such as tracking of a source of each medium component that is used in a process for culturing recombinant *Escherichia coli* may be required.

Therefore, for solving these problems, it is necessary to provide a culture substrate which is capable of adhering cells without requiring coating of a cell adhesive factor and which is capable of culturing and growing cells.

CITATION LIST

Patent Document

PTD 1: National Patent Publication No. 2009-540865
PTD 2: National Patent Publication No. 2010-523118
PTD 3: Japanese Patent Laying-Open No 2014-117190
PTD 4: National Patent Publication No. 2012-503688

SUMMARY OF INVENTION

Technical Problems

An object of the present invention is to provide a hollow-fiber membrane which does not require a pretreatment such as a coating treatment with a cell adhesion factor or surface modification by an electron beam or the like and which is capable of adhering and culturing cells, and a method for culturing cells using the hollow-fiber membrane.

Solutions to Problems

The present inventors have extensively conducted studies for solving the above-described problems, and resultantly found that the above-described problems can be solved by the following means, leading to attainment of the present invention.

That is, the present invention includes the following constitutions.

1. A hollow-fiber membrane for cell culture which is to be used as a culture substrate for adhesive cells, in which the hollow-fiber membrane includes a hydrophobic polymer and a hydrophilic polymer, a content of the hydrophilic polymer in a whole hollow-fiber membrane is more than 0% by mass and less than 1% by mass, and a content of the hydrophilic polymer on a surface of the hollow-fiber membrane is more than 0% by mass and less than 10% by mass.

2. The hollow-fiber membrane according to 1, in which the hydrophobic polymer is at least one selected from the group consisting of polyether sulfone, polysulfone, polyvinylidene fluoride and polyethylene.

3. The hollow-fiber membrane according to 1 or 2, in which the hydrophilic polymer is at least one selected from the group consisting of polyvinyl pyrrolidone, polyethylene glycol, polyvinyl alcohol, carboxymethyl cellulose and starch.

4. A hollow-fiber module for cell culture which contains a hollow fiber bundle obtained by bundling more than one hollow-fiber membrane according to any one of 1 to 3.

5. A method for culturing cells using the hollow-fiber module according to 4 as a cell culture container.

6. A cell culture apparatus including the hollow-fiber module according to 4 as a cell culture container.

Advantageous Effects of Invention

According to the present invention, it is possible to provide a hollow-fiber membrane as a culture substrate which does not require a coating treatment with a cell adhesion factor. In addition, when the hollow-fiber membrane of the present invention is used, it is possible to construct and provide a cell culture system capable of safely, easily and efficiently culturing various kinds of cells such as mesenchymal stem cells.

DESCRIPTION OF EMBODIMENTS

In the present invention, the term "hydrophobic" means being hardly compatible with water (the term "hydrophilic" means being easily compatible with water). For example, a contact angle is an example of an index that objectively indicates whether a polymer is hydrophobic or hydrophilic. When a tangent line is drawn to a curved surface of a liquid from a part of a water droplet placed on a surface of a polymer sheet, film or membrane, where a solid, a liquid and a gas (that is generally air, and hereinafter referred to as air) are in contact with the water droplet, the contact angle is defined as an angle formed by the tangent line and a solid surface, and is, for example, a value determined in accordance with the sessile drop method in JIS R3257 (1999). A smaller contact angle means being more hydrophilic, and a larger contact angle means being more hydrophobic. In the present invention, polymers having a contact angle of 70 degrees or more are classified as being hydrophobic, and polymers having a contact angle of less than 70 degrees are classified as being hydrophilic.

When a porous membrane composed only of a hydrophobic polymer is dried, the surface tension makes it impossible to introduce water into pores unless a high pressure is applied. That is, the membrane cannot be easily rewetted. In particular, this tendency is noticeable for membranes having submicron-sized or smaller pores. Thus, a hydrophobic membrane is not suitable for solid-liquid separation applications with water as a medium, and is suitably used for applications for passage of a gas, such as solid-gas separation and gas-liquid separation. Accordingly, when a membrane composed only of a hydrophobic material is to be used for solid-liquid separation, the membrane can be used only by a method in which the membrane is wetted a liquid having a low surface tension (e.g. alcohol) in advance, and the liquid is introduced into the pore, and then replaced by water. On the other hand, in the case of a membrane sufficiently containing a hydrophilic material on pore surfaces, it is possible to replace the liquid by water directly from a dry state because the membrane has a low surface tension (i.e. low contact angle) with water. Thus, when used for solid-liquid separation, the membrane is easily pre-treated, and thus suitably used.

In the present invention, the hydrophobic polymer to be used as a material of the hollow-fiber membrane is not particularly limited as long as it can be structured to be permeable to solutions and low-molecular substances, and polyether sulfone, polysulfone, polyvinylidene fluoride, polyethylene and the like can be suitably used. The membrane may be mainly composed of a derivative of such a polymer. Among the above-mentioned hydrophobic polymers, polyether sulfone and polysulfone that are polysulfone-based polymers are more preferable. The polysulfone-based polymer is mainly composed of repeating units represented by the following chemical formulae 1 and 2.

[Chemical Formula 1]

[Chemical Formula 2]

In the present invention, examples of the hydrophilic polymer include water-soluble polymers such as polyethylene glycol, polyvinyl alcohol, polyvinyl pyrrolidone (hereinafter, sometimes abbreviated as PVP), carboxymethyl cellulose and starch, and copolymers and derivatives thereof. Among them, PVP is preferable from the viewpoint of compatibility with a polysulfone-based polymer and a past use record as a fluid treatment membrane. One of these polymers may be used alone, or two or more of these polymers may be mixed and used. The molecular weight of PVP is preferably 10 to 100 in terms of a K value. Specifically, for example, Luvitec (trade name) K17, K30, K60, K80, K85 and K90 that are commercially available from BASF Company are preferable, and among them, Luvitec (trade name) K60, K80, K85 and K90 are more preferable.

In the present invention, it is preferable that in the hollow-fiber membrane, the content of the hydrophilic polymer in the whole membrane is more than 0% by mass and less than 1% by mass, and the content of the hydrophilic polymer on a membrane surface is more than 0% by mass and less than 10% by mass. The content of the hydrophilic polymer in the while membrane is determined by analysis in nuclear magnetic resonance spectroscopy (NMR). The content of the hydrophilic polymer on the membrane surface is determined using Electron Spectroscopy for Chemical Analysis (ESCA). In ESCA, the content of hydrophilic polymer can be measured at a depth of about 10 nm from the membrane surface.

In the present invention, a protein such as fibronectin is quickly adsorbed to the hollow-fiber membrane in which the content of the hydrophilic polymer in the whole membrane is more than 0% by mass and less than 1% by mass, and the content of the hydrophilic polymer on the membrane surface is more than 0% by mass and less than 10% in a short time when a liquid medium (hereinafter, sometimes referred to simply as a medium) is brought into contact with the surface of the hollow-fiber membrane. This gives an environment in which adhesive cells such as stem cells easily adhere to the surface of the hollow-fiber membrane, and therefore thereafter, the cells can be efficiently grown.

The amount of a protein attached to the surface of the hollow-fiber membrane increases as the content of the hydrophilic polymer on the membrane surface decreases, but when the content of the hydrophilic polymer is excessively low, the membrane surface is not wetted with water, and therefore in culture of cells, a hydrophilization treatment with a 40% ethanol solution or the like is required before passage of the cells through a medium. Thus, there is a problem from the viewpoint of convenience for use in culture. In addition, when the content of the hydrophilic polymer is excessively high, there is the problem that a protein is hardly attached, and adhesion of cells is accordingly reduced.

In the present invention, the size of the hollow-fiber membrane is not particularly limited, but the inner diameter is preferably 100 to 1000 μm, and more preferably about 150 to 500 μm. The thickness of the hollow-fiber membrane is not particularly limited, and it may be within such a range that the hollow-fiber membrane maintains a moderate strength, and permeability of a substance is not significantly hindered. The thickness of the hollow-fiber membrane is preferably 10 to 150 μm, more preferably about 20 to 100 μm.

In the present invention, the pore size of the hollow-fiber membrane is not particularly limited as long as the pore is a through-hole through which cells do not pass, but medium components such as water, salts and proteins pass. When consideration is given to culture of cells, it is desirable to have a relatively large pore size ensuring that substances are efficiently exchanged, and the average pore size is preferably 0.001 to 0.5 μm more preferably about 0.01 to 0.1 μm. The molecular weight cutoff (the molecular weight at which the sieving coefficient is less than 0.1) is preferably 1 to 1,000,000, more preferably about 2 to 200,000. Further, the pore size of the membrane is also affected by adsorption of various kinds of biological components and clogging which are associated with culture. That is, an optimal design should be made in view of an interaction with these substances.

In the present invention, the water permeability of the hollow-fiber membrane is not particularly limited, but is preferably 10 to 1000 mL/m$^2$/hr/mmHg, more preferably 20 to 500 mL/m$^2$/hr/mmHg. When the water permeability is excessively small, it is impossible to perform sufficient material movement. On the other hand, it is not preferable that the water permeability is excessively large because when a medium or the like is caused to flow into an inner cavity and an outer cavity of the hollow-fiber membrane, a pressure difference is produced between the membranes, so that filtration spontaneously occurs, or a distribution (concentration difference) of flows (medium components) is generated in the length direction of the hollow-fiber membrane.

When the hollow-fiber membrane according to the present invention comes into contact with a medium, a protein contained in the medium is adsorbed as described above, and it is not preferable that as a result, the water permeability and the substance permeability of the membrane during cell culture are impaired. The hollow-fiber membrane according to the present invention is capable of attaching a protein that promotes cell adhesion, and also efficiently exchanging substances with cells during culture, e.g. supplying nutrients and gases to the cells and removing wastes from the cells, through the membrane as a culture substrate.

In the present invention, use of the hollow-fiber membrane as a culture substrate has an advantage that exchange of substances through a membrane, which cannot be performed by normal Petri dish or flask culture, can be performed, so that it is possible to efficiently supply nutrients, oxygen and carbon dioxide (concentration adjustment) and remove wastes. At the same time, however, necessary components may be excessively removed, and therefore by optimally controlling the pore size, a culture environment in the vicinity of cells can be made favorable to improve culture efficiency. It is to be noted that the pore size (substance permeability) is very easily affected by proteins and in the medium and cell-secreted proteins (e.g. fibronectin that mainly forms a cell-adhesive extracellular matrix). Therefore, it is necessary that substances be sufficiently exchanged even under the influence of these proteins. In conventional techniques, hydrophilization of a membrane is preferably performed for compensating for the above-mentioned difficulty. However, in order to improve the adhesion of cells, it is necessary to coat a base with highly purified cell adhesion factor over a long period of time (about 1 day). In the present invention, both quick attachment of the protein to membrane surface and exchange of substances are attained by using a hollow-fiber membrane excellent in balance between hydrophobicity and hydrophilicity.

(Hollow-Fiber Module)

In the present invention, for example, a hollow-fiber module as a cell culture container can be prepared by storing several tens to several tens of thousands of hollow fiber bundles in a cylindrical container. In the hollow-fiber module, depending on the size of the hollow-fiber membrane, a large culture area per unit volume can be secured, and culture operations can be simplified, so that it is possible to perform cell culture with high safety while saving a space.

Figure 1:
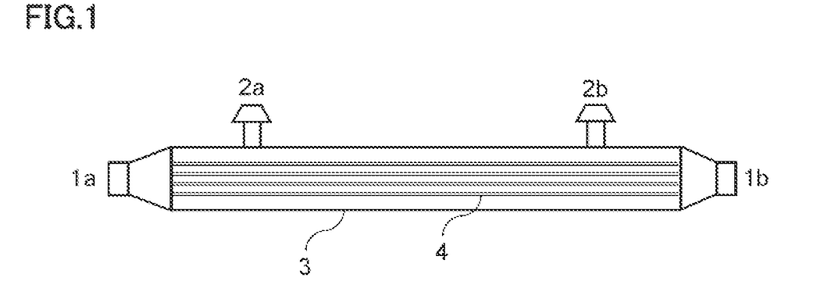
FIG. 1 is a schematic view showing one example of a hollow-fiber module according to the present invention.

The configuration of the module including a hollow-fiber membrane is not particularly limited, and mention is made of, for example, a configuration in which a necessary number of hollow-fiber membranes 4 are appropriately bundled and packed in a module case 3 having four opening sections (end conduits and side conduits) as shown in FIG. 1. Among the four opening sections, two end conduits 1a and 1b are each bonded and fixed to an end of the module case by an appropriate sealing material (e.g. a polyurethane-based potting agent) so as not to close the hollow portion of the hollow-fiber membrane while an inner cavity (hollow portion) and an outer cavity of each hollow-fiber membrane are separated at each of both ends of the hollow-fiber bundle, and a liquid or the like introduced from one end conduit 1a or 1b passes through the inner cavity of the hollow-fiber membrane to be discharged from the other end conduit 1b or 1a (i.e. flows in one direction). On the other hand, among the openings, two side conduits 2a and 2b are connected to a space inside module case 3 and outside the hollow-fiber bundle (hereinafter, also referred to simply as an "outer cavity"), and a liquid or the like introduced from one end conduit 2a or 2b passes through the outer cavity of the module to be discharged from the other end conduit 2b or 2a (i.e. flows in one direction).

When the hollow-fiber module is used as a cell culture container in the present invention, cells may be cultured either in the inner cavity or in the outer cavity of the hollow-fiber membrane, but it is preferable to culture cells in the inner cavity. For example, when cells are cultured in the inner cavity, a cell suspension liquid is injected from the end conduit into the inner cavity to seed the cells on the inner surface of the hollow-fiber membrane, and after the cells are seeded, the cell suspension liquid is replaced by a medium, and the medium is perfused, so that cells are cultured for a certain period of time. It is preferable that in the meantime, the medium is also injected into the outer cavity from the side conduit, and perfused simultaneously.

The liquid medium has a role of supplying necessary nutrients and gases such as oxygen and carbon dioxide to cells. It is preferable that during the culture period, the medium is continuously supplied to both the inner cavity and the outer cavity in one direction for exchanging gases, supplying nutrients to cells and removing wastes. Here, the medium can be circulated or supplied and discharged at an appropriate speed by using a pump or the like.

The hollow-fiber module is sterilized by an appropriate method, and supplied to the market. The sterilization method is not particularly limited, and examples thereof include high-pressure steam sterilization, electron beam sterilization, radiation sterilization and ethylene oxide gas sterilization.

In the present invention, a fresh medium can always be supplied to cells by using the hollow-fiber module as a culture container, and therefore the medium replacement operation necessary in use of a Petri dish, a multi-stage flask or the like as a culture container is unnecessary, so that the actual working time of operators and the risk of contamination can be reduced.

(Cells to be Cultured)

In the present invention, cells to be cultured are not particularly limited, but adhesive animal cells are suitable. The source of cells is not particularly limited, and cells derived from any animal such as a human, a pig, a dog, a mouse or the like can be used. In addition, either first stage culture cells or established cells can be targeted as adhesive animal cells. In addition, the adhesive animal cells may be primary cells such as epidermal keratinocytes, vascular endothelial cells, fibroblasts and hepatocytes, stem cells such as embryonic stem cells, artificial pluripotent stem cells, mesenchymal stem cells, adipose precursor cells and hepatic stem cells, and precursor cells. In addition, these cells may be cells into which a foreign gene is introduced before culture, or cells that are stimulated with a stimulating factor such as an antibody or a ligand, and processed beforehand.

(Cell Culture Apparatus)

Figure 2:
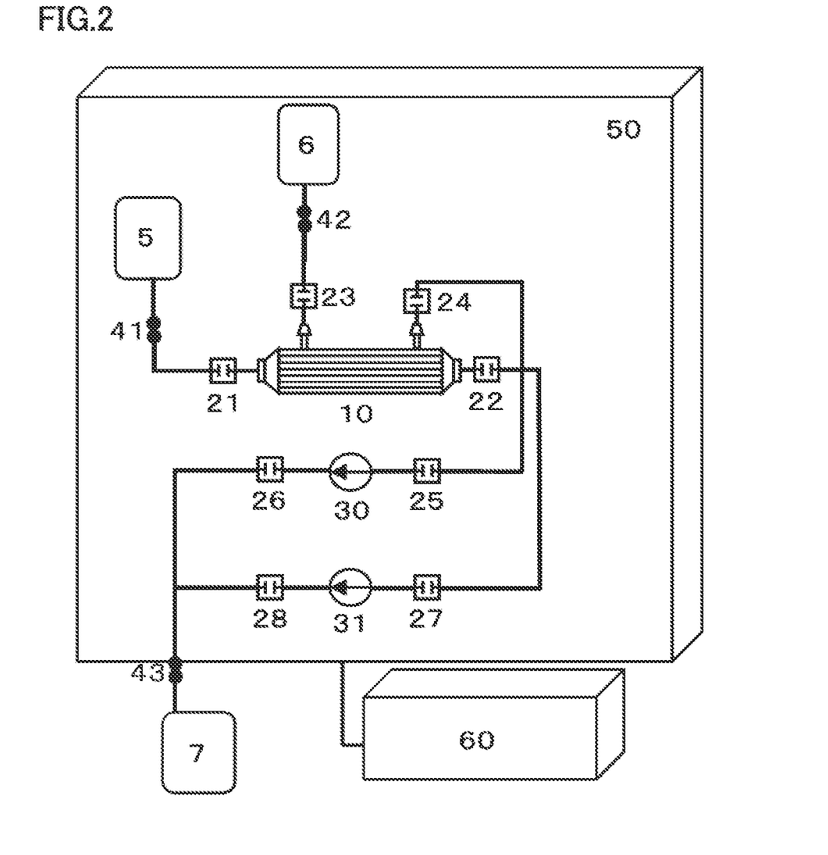
FIG. 2 is a schematic view showing one example of a cell culture apparatus according to the present invention.

FIG. 2 shows one example of a configuration of a cell culture apparatus according to the present invention. In FIG. 2, reference numerals 5 and 6 each denote a liquid medium storage container (e.g culture bag). From a liquid medium storage container 5, a circuit is connected to the end conduit (1a in FIG. 1) of a cell culture container 10 (hollow-fiber module) through a sterile connector 41 and a valve 21, so that a medium in liquid medium storage container 5 can be transferred to the inner cavity of cell culture container 10. On the other hand, from a liquid medium storage container 6, a circuit is connected to the side conduit (2a in FIG. 1) of cell culture container 10 through a sterile connector 42 and a valve 23, so that a medium in liquid medium storage container 6 can be transferred to the outer cavity of cell culture container 10.

From the end conduit (1b in FIG. 1) of cell culture container 10, a circuit is connected to a waste liquid collection container (or cell collection container) 7 through a pump 31, so that the medium passing through cell culture container 10 can be discarded. By pump 31 provided in the circuit, the flow rate or the like in each of supply of a liquid (medium etc.) from liquid medium storage container 5 to cell culture container 10, discharge of the liquid from cell culture container 10, disposal of the liquid, and the like can be controlled. On the other hand, from the side conduit (2b in FIG. 1) of cell culture container 10, a circuit is connected to waste liquid collection container 7 through a pump 30, so that the medium passing through cell culture container 10 can be discarded. By pump 30 provided in the circuit, the flow rate or the like in each of supply of a liquid (medium etc.) from liquid medium storage container 6 to cell culture container 10, discharge of the liquid from cell culture container 10, disposal of the liquid, and the like can be controlled.

In FIG. 2, it is preferable that at least liquid medium storage containers 5 and 6 and cell culture container 10 are stored in a $CO_2$ incubator 50. In addition, an operation controller (operation panel) 60 for controlling and monitoring the above-described operations and processes may be added.

(Culture of Cells)

When the hollow-fiber membrane according to the present invention is used, and cells are cultured in, for example, the inner cavity of the hollow-fiber membrane, cells can be seeded by using the hollow-fiber module, and causing a cell-suspended liquid to flow from one of the end conduits is into the inner cavity of the hollow-fiber membrane. Cells can be cultured and grown by continuously or intermittently feeding the medium into the hollow-fiber module installed in the incubator after the cells are left standing for a certain period of time to adhere to the surface of the hollow-fiber membrane. In addition, the medium may be one that is determined according to the type of cultured cells, and commonly used as a medium for the cells. The culture method according to the present invention can also be used for serum-free culture.

In addition, in supply of the medium, different liquid medium storage containers may be used for the inner cavity and the outer cavity, or the medium may be distributed and supplied to both the inner cavity and the outer cavity from one container. Here, the medium composition of the inner cavity and the medium composition of the outer cavity may be the same or different. In addition, the medium flow rate in the inner cavity and the medium flow rate in the outer cavity may be the same or different, but it is more preferable to increase the medium flow rate in the outer cavity.

The flow rate of the medium during cell culture is not particularly limited, but it is preferable to appropriately adjust the flow rate as cells are grown. Particularly in the initial stage of culture until the start of a logarithmic growth phase, it is necessary to strictly control the flow rate for supply of nutrients and maintenance of a microenvironment around cells. That is, when the flow rate is excessively low, nutrients are not sufficiently supplied to cells, and the cells are difficult to grow. Conversely, when the flow rate is excessively high, a change in environment around cells increases. Preferably, a change in concentration of glucose and lactic acid in the medium is monitored, and the flow rate is adjusted on the basis of the results of the monitoring.

In the present invention, it is preferable that the medium in the hollow-fiber module flows in one direction. Specifically, mention is made of a configuration in which the medium is introduced from one end conduit, and flows toward the opposite conduit (outlet) at all times. A circulation type may be employed in which a medium discharged from the hollow-fiber module once is introduced from an inlet again. At least one of the inner cavity and the outer cavity of the hollow-fiber membrane may be of circulation type, or both of the cavities may be of circulation type.

In the present invention, rotation, shaking, rolling or the like of the hollow-fiber module may be performed after cell seeding and/or during cell culture. It is preferable that such an operation is performed because, for example, cells seeded in the inner cavity of the hollow-fiber membrane are uniformly dispersed on and adhered to the surface of the hollow-fiber membrane, bubbles are easily removed when generated, and nutrients of the medium are evenly distributed to cultured cells.

(Collection of Cells)

In the present invention, the means for recovering cells cultured using the hollow-fiber membrane is not particularly limited. For example, when cells are cultured in the inner cavity of the hollow-fiber membrane, perfusion of the medium is stopped, and divalent cation-free phosphate buffered saline (PBS) is then perfused for a certain period of time for removing the medium existing in the inner cavity and the outer cavity of the hollow-fiber membrane, so that the medium is sufficiently replaced by PBS. Next, PBS is removed, the inner cavity and the outer cavity of the hollow-fiber membrane are filled with a solution of protease such as trypsin, and the cells are incubated for a certain period of time. By such a treatment, the cultured cells are separated from the hollow-fiber membrane, the medium or the like is then caused to flow into the inner cavity of the hollow-fiber membrane, and thus discharged, so that the cells can be collected.

EXAMPLES (Measurement of Water Permeability)

Pure water in an amount 50 times the internal volume of a module case was introduced from one end conduit (1a in FIG. 1) to a module including a hollow-fiber membrane in a dry state, and discharged from the other end conduit (1b in FIG. 1), so that the membrane was sufficiently washed, and membrane pores and hollow portions were replaced with the pure water. Thereafter, for the outer cavity of the hollow-fiber membrane, similarly pure water in an amount 50 times the inner volume of the module case was caused to flow from outer cavity 2a to outer cavity 2b in FIG. 1 to perform washing. Pure water kept at 25° C. was added in a pressure tank, the pure water was fed to an inner cavity of the module kept at a certain temperature in a thermostatic bath at 25° C. while the pressure was controlled by a regulator, an outlet (1b) and a permeation-side outlet (2b) were closed, and the amount of the filtrate flowing out from the permeation side (2a) of the membrane was measured for a certain period of time. The pressure difference between membranes was defined as a pressure applied to the module inlet side (equal to a pressure applied to the tank), and measured at 100 mmHg. The water permeability ($mL/m^2/hr/mmHg$) of the hollow-fiber membrane was calculated using the area of a membrane permeation portion of the module used (membrane area based on the inner diameter of the hollow-fiber membrane).

In addition, a 40 vol % EtOH solution in an amount 50 times the internal volume of a module case was introduced from one end conduit (1a in FIG. 1) to another module including a hollow-fiber membrane in a dry state, and discharged from the other end conduit (1b), so that the membrane was sufficiently washed, and membrane pores and hollow portions were replaced with 40 vol % EtOH. Thereafter, for the outer cavity of the hollow-fiber membrane, similarly 40 vol % EtOH solution in an amount 50 times the inner volume of the module case was caused to flow from outer cavity 2a to outer cavity 2b in FIG. 1 to perform washing. Thereafter, the washing with pure water and liquid replacement were performed again, and the EtOH was replaced by pure water, and the water permeability after hydrophilization treatment was measured by the above-described method.

(Filtration Experiment)

(1) A test liquid was prepared in the following manner. Specifically, inulin (molecular weight 5,500, manufactured by nacalai tesque), dextran T10 (molecular weight: 10,000, Sigma-Aldrich Company) and dextran T40 (molecular weight: 40,000, Sigma-Aldrich Company) were dissolved in injection distilled water (Otsuka Pharmaceutical Co., Ltd.) to prepare aqueous solutions each having a concentration of 1,000 ppm, and the aqueous solutions were used as test liquids in subsequent experiments.

(2) Priming was performed by passage of each test liquid through the inner cavity of the hollow-fiber membrane of the hollow-fiber module, distilled water or each test liquid kept at 25° C. was then filtered for a certain period of time by application of a pressure of 100 mmHg, and the sieving coefficient (hereinafter, referred to as SC) was determined. For sampling of the liquid, the time point at which the filtrate started to appear was set to a basic point, sampling was started two minutes after the basic point, and the whole amount of the filtrate of several minutes (3 to 4 minutes) was collected. SC is defined as a ratio of the concentration of dextran etc. in the permeated liquid to the concentration of dextran etc. in the supplied liquid. The concentration of dextran etc. is quantitatively determined by a usual method such as a GPC method, a colorimetric method (anthrone-sulfuric acid method) or the like, and when a monodisperse dextran reagent, the molecular weight of which is specified as in the present method, is used, the convenient colorimetric method can be used. In the experiment, the water permeability of each test liquid was also measured.

(3) Next, the inner cavity of the hollow-fiber membranes of each hollow-fiber module was filled with Dulbecco's Modified Eagle's Medium (DMEM) containing fetal bovine serum in such a manner in an amount of 10 vol %, the hollow-fiber module was left standing at 25° C. for 30 minutes, the filling liquid was then removed, the hollow-fiber module was washed with pure water in an amount about 100 times the volume of the inner cavity portion of the hollow-fiber membrane, each test liquid was filtered in the same manner as in (2) above, and the SC and the water permeability were determined. The change ratio is a ratio of the value after contact to the value before contact.

(Measurement of Inner Diameter and Thickness)

The inner diameter, the outer diameter and the film thickness of the hollow-fiber membrane are determined in the following manner: an appropriate number of hollow-fiber membranes are caused to pass through φ3 mm holes at the center of a slide glass in such a manner that the hollow-fiber membranes do not fall off the hollow-fiber membranes are cut by a razor at the upper and lower surfaces of the slide glass to obtain hollow-fiber membrane cross-section samples, and minor diameters and major diameters of the hollow-fiber membrane cross-sections are then measured using a projector Nikon-V-12A. For a hollow-fiber membrane having a shape close to complete circle, minor diameters and major diameters in two directions were measured, and the arithmetic average values of the minor diameters and the major diameters were defined as an inner diameter and an outer diameter of one hollow-fiber membrane cross-section. In addition, the thickness was calculated in accordance with the formula: (outer diameter−inner diameter)/2. For five cross-sections including the maximum and the minimum, measurements were made in the same manner as described above, and the average values of the measurements were defined as an inner diameter, an outer diameter and a thickness, respectively.

(Measurement of PVP Content of Surface of Hollow-Fiber Membrane)

The PVP content on the surface of the hollow-fiber membrane was determined by X-ray photoelectron spectroscopy (ESCA method). A measurement method using a polysulfone-based polymer as a hydrophobic polymer is shown as an example.

One hollow-fiber membrane was obliquely cut by a razor so as to expose a part of the inner surface thereof and attached to a sample table so that it was possible to measure the inner surface. Measurement conditions are as follows.

Measuring device: ULVAC-FIE ESCA 5800
Excited X-ray: MgK α ray
X-ray power: 14 kV, 25 mA
Photoelectron escape angle: 45°
Analytical diameter: 400 μmφ
Path energy: 29.35 eV
Resolution: 0.125 eV/step
Vacuum degree: about $10^{-7}$ Pa or less From the measured value of nitrogen (N) and the measured value of sulfur (S), the PVP content on the surface of the hollow-fiber membrane was calculated in accordance with the following formula.

<PES (Polyether Sulfone) Membrane Containing PVP>

$$\text{PVP content (Hpvp) [\%]}=100\times(N\times111)/(N\times111+S\times232)$$

<PSf (Polysulfone) Membrane Containing PVP>

$$\text{PVP content (Hpvp) [\%]}=100\times(N\times111)/(N\times111+S\times442)$$

(Measurement of PVP Content of Whole Hollow-Fiber Membrane)

The hollow-fiber membrane was dissolved in DMSO-d6, and 1H-NMR was measured at 60° C. Avance-500 manufactured by Brucker Company was used for the measurement. From the integral intensity ratio of a peak (a) derived from an aromatic ring of the polysulfone-based polymer in the vicinity of 7.2 ppm and a peak (b) derived from a pyrrolidone ring of PVP in the vicinity of 2.0 ppm in a 1H-NMR spectrum, the content of PVP was calculated in accordance with the following formula.

$$\text{PVP content [\% by mass]}=\{(b/nb)\times111\times100\}/\{(a/na)\times Ma+(b/nb)\times111\}$$

Ma represents a molecular weight of the repeating unit of the polysulfone-based polymer, 111 represents a molecular weight of the repeating unit of PVP, na represents the number of protons of a contained in the repeating unit, nb is the number of protons of b contained in the repeating unit.

Example 1

(Preparation of Hollow-Fiber Membrane and Hollow-Fiber Module 1)

20% by mass of polyether sulfone (PES) (4800 P manufactured by Sumitomo Chemical Company, Limited), 0.2% by mass of polyvinyl pyrrolidone (PVP) (K-90 manufactured by BASF Company), 35.91% by mass of N-methyl pyrrolidone (NMP), and 43.89% by mass of triethylene glycol (TEG) were mixed and dissolved, the resulting solution was defoamed to obtain a deposition solution, a mixed liquid of 13.5% by mass of NMP, 16.5% by mass of TEG and 70% by mass of water was provided as a core liquid, the deposition solution and the core liquid were discharged, respectively, from the outside and the inside of a double-tube orifice heated to 70° C., and guided through a 30 cm idle running section into a coagulation bath including water at 75° C., so that a hollow-fiber membrane was formed. The hollow-fiber membrane was washed with water, and then wound up in the form of a bundle. The fiber bundle was cut, and then subjected to forced-air drying at 60° C. The dried hollow-fiber membrane had an inner diameter of 200 μm, an outer diameter of 300 μm and a thickness of 50 μm.

Next, a hollow-fiber module was prepared in the following manner. 100 hollow-fiber membranes were inserted in a cylindrical polycarbonate module case having an inner diameter of 1 cm and a length of 10 cm, and then each fixed at both ends to the module case with a polyurethane-based potting agent so as not to close a hollow portion of the hollow-fiber membrane, and thus a hollow-fiber module 1 having a shape as shown in FIG. 1 was prepared.

Example 2

(Preparation of Hollow-Fiber Membrane and Hollow-Fiber Module 2)

20% by mass of PES, 0.5% by mass of PVP, 35.77% by mass of NMP and 43.73% by mass of TEG were mixed and dissolved, and the resulting solution was defoamed to obtain a deposition solution, a mixed liquid of 13.5% by mass of NMP, 16.5% by mass of TEG and 70% by mass of water was provided as a core liquid, the deposition solution and the core liquid were discharged, respectively, from the outside and the inside of a double-tube orifice heated to 70° C., and guided through a 30 cm idle running section into a coagulation bath including water at 75° C., so that a hollow-fiber membrane was formed. The hollow-fiber membrane was washed with water, and then wound up in the form of a bundle. The fiber bundle was cut, and then subjected to forced-air drying at 60° C. The dried hollow-fiber membrane had an inner diameter of 200 μm, an outer diameter of 300 μm and a thickness of 50 μm.

Using the obtained hollow-fiber membranes, a hollow-fiber module 2 was prepared in the same manner as in Example 1.

Example 3

(Preparation of Hollow-Fiber Membrane and Hollow-Fiber Module 3)

20% by mass of PES, 1.0% by mass of PVP, 35.55% by mass of NMP and 43.45% by mass of TEG were mixed and dissolved, the resulting solution was defoamed to obtain a deposition solution, a mixed liquid of 13.5% by mass of NMP, 16.5% by mass of TEG and 70% by mass of water was provided as a core liquid, the deposition solution and the core liquid were discharged, respectively, from the outside and the inside of a double-tube orifice heated to 70° C., and guided through a 30 cm idle running section into a coagulation bath including water at 75° C., so that a hollow-fiber membrane was formed. The hollow-fiber membrane was washed with water, and then wound up in the form of a bundle. The fiber bundle was cut, and then subjected to forced-air drying at 60° C. The obtained hollow-fiber membrane had an inner diameter of 200 µm, an outer diameter of 300 µm and a thickness of 50 µm.

Next, Using the obtained hollow-fiber membranes, a hollow-fiber module 3 was prepared in the same manner as in Example 1.

Comparative Example 1

(Preparation of Hollow-Fiber Membrane and Hollow-Fiber Module 4)

19.5% by mass of PES, 1.5% by mass of PVP, 35.55% by mass of NMP and 43.45% by mass of TEG were mixed and dissolved, the resulting solution was defoamed to obtain a deposition solution, a mixed liquid including 13.5% by mass of NMP, 16.5% by mass of TEG and 70% by mass of water was provided as a core liquid, the deposition solution and the core liquid were discharged, respectively, from the outside and the inside of a double-tube orifice heated to 70° C., and guided through a 30 cm idle running section into a coagulation bath including water at 75° C., so that a hollow-fiber membrane was formed. The hollow-fiber membrane was washed with water, and then wound up in the form of a bundle. The fiber bundle was cut, and then subjected to forced-air drying at 60° C. The obtained hollow-fiber membrane had an inner diameter of 200 µm, an outer diameter of 300 µm and a thickness of 50 µm.

Using the obtained hollow-fiber membranes, a hollow-fiber module 4 was prepared in the same manner as in Example 1.

Comparative Example 2

(Preparation of Hollow-Fiber Membrane and Hollow-Fiber Module 5)

16% by mass of PES, 3.0% by mass of PVP, 76.0% by mass of dimethyl acetamide (DMAc) and 5% by mass of water were mixed and dissolved, the resulting solution was defoamed to obtain a deposition solution, a 50 mass % DMAc aqueous solution was provided as a core liquid, the deposition solution and the core liquid were discharged, respectively, from the outside and the inside of a double-tube orifice heated to 70° C., and guided through a 50 cm idle running section into a coagulation bath including water at 75° C., so that a hollow-fiber membrane was formed. The hollow-fiber membrane was washed with water, then wound up in the form of a bundle, and dried at 60° C. The obtained hollow-fiber membrane had an inner diameter of 200 µm, an outer diameter of 280 µm and a thickness of 40 µm.

Using the obtained hollow-fiber membranes, a hollow-fiber module 5 was prepared in the same manner as in Example 1.

Comparative Example 3

(Preparation of Hollow-Fiber Membrane and Hollow-Fiber Module 6)

16% by mass of PES, 5.0% by mass of PVP, 74.0% by mass of DMAc and 5% by mass of water were mixed and dissolved, the resulting solution was defoamed to obtain a deposition solution, a 50 mass % DMAc aqueous solution was provided as a core liquid, the deposition solution and the core liquid were discharged, respectively, from the outside and the inside of a double-tube orifice heated to 70° C., and guided through a 50 cm idle running section into a coagulation bath including water at 75° C., so that a hollow-fiber membrane was formed. The hollow-fiber membrane was washed with water, then wound up in the form of a bundle, and dried at 60° C. The obtained hollow-fiber membrane had an inner diameter of 200 µm, an outer diameter of 280 µm and a thickness of 40 µm.

Using the obtained hollow-fiber membranes, a hollow-fiber module 6 was prepared in the same manner as in Example 1.

Comparative Example 4

(Preparation of Hollow-Fiber Membrane and Hollow-Fiber Module 7)

20% by mass of PES, 36% by mass of NMP and 44% by mass of TEG were mixed and dissolved, the resulting solution was defoamed to obtain a deposition stock solution, a mixed liquid including 13.5% by mass of NMP, 16.5% by mass of TEG and 70% by mass of water was provided as a core liquid, the deposition solution and the core liquid were discharged, respectively, from the outside and the inside of a double-tube orifice heated to 70° C., and guided through a 300 mm idle running section into a coagulation bath including water at 75° C., so that a hollow-fiber membrane was formed. The hollow-fiber membrane was washed with water, and then wound up in the form of a bundle. The fiber bundle was cut, and then subjected to forced-air drying at 60° C. The obtained hollow-fiber membrane had an inner diameter of 200 µm, an outer diameter of 300 µm and a thickness of 50 µm.

Using the obtained hollow-fiber membranes, a hollow-fiber module 7 was prepared in the same manner as in Example 1.

For the hollow-fiber membranes prepared in Examples 1 to 3 and Comparative Examples 1 to 4, the PVP content in the whole hollow-fiber membrane and the PVP content on the surface of the hollow-fiber membrane were measured by nuclear magnetic resonance spectroscopy (NMR), electron spectroscopy for chemical analysis (ESCA). For each hollow-fiber module, the water permeability was measured by the method described above. The results are shown in Table 1.

TABLE 1

|  | PVP content in whole hollow-fiber membrane (%) | PVP content on surface of hollow-fiber membrane (%) | Water permeability ($mL/m^2/hr/mmHg$) | After treatment with 40% EtOH |
|---|---|---|---|---|
| Example 1 | 0.3 | 4.3 | 167 | 330 |
| Example 2 | 0.5 | 7 | 175 | 327 |
| Example 3 | 0.9 | 9.9 | 198 | 324 |

TABLE 1-continued

|  | PVP content in whole hollow-fiber membrane (%) | PVP content on surface of hollow-fiber membrane (%) | Water permeability (mL/m²/hr/mmHg) | After treatment with 40% EtOH |
|---|---|---|---|---|
| Comparative example 1 | 1.4 | 14.8 | 235 | 280 |
| Comparative example 2 | 2.8 | 20.1 | 271 | 285 |
| Comparative example 3 | 3.2 | 24.4 | 258 | 272 |
| Comparative example 4 | 0 | 0 | Measurement impossible | 340 |

The results of the filtration experiment are shown in Tables 2 and 3. Table 2 shows a change in sieving coefficient (SC) before and after the hollow-fiber module is brought into contact with the medium described in (3). On the other hand. Table 3 shows a change in water permeability (mL/m²/hr/mmHg) before and after the hollow-fiber module is brought into contact with the medium described in (3).

In Examples 1 to 3, the permeability tends to be slightly lower for a polymer having a molecular weight of 40,000 or more as compared to Comparative Examples, but a favorable substance permeability is exhibited in each of Examples 1 to 3.

When a general medium: Dulbecco's Modified Eagle's Medium (DMEM) containing fetal bovine serum in an amount of 10 vol % was brought into contact with these hollow-fiber membranes for a certain period of time, the membrane properties of each hollow-fiber membrane were changed. Specifically, in Examples 1 to 3, the sieving coefficient (SC) and the water permeability are more significantly changed as compared to Comparative Examples 1 to 3. This is because a protein contained in the medium is more efficiently attached to the surface of a hydrophobic polymer membrane. In addition, since a certain level of substance permeability is retained even after the protein is attached, cell culture is not affected at all. This showed that the hollow-fiber membranes (hollow-fiber modules) of Examples 1 to 3 had properties as a culture substrate (culture container) excellent in cell adhesion.

TABLE 2

|  | SC inulin | | | SC dextran T10 | | | SC dextran T40 | | |
|---|---|---|---|---|---|---|---|---|---|
|  | Before contact with medium | After contact with medium | Change ratio | Before contact with medium | After contact with medium | Change ratio | Before contact with medium | After contact with medium | Change ratio |
| Example 1 | 0.947 | 0.939 | 0.992 | 0.959 | 0.730 | 0.761 | 0.859 | 0.301 | 0.350 |
| Example 2 | 0.942 | 0.931 | 0.988 | 0.948 | 0.726 | 0.766 | 0.815 | 0.312 | 0.383 |
| Example 3 | 0.938 | 0.928 | 0.989 | 0.948 | 0.726 | 0.766 | 0.815 | 0.312 | 0.383 |
| Comparative example 1 | 0.966 | 0.964 | 0.998 | 0.951 | 0.816 | 0.858 | 0.745 | 0.395 | 0.530 |
| Comparative example 2 | 0.972 | 0.975 | 1.003 | 0.948 | 0.853 | 0.900 | 0.602 | 0.381 | 0.633 |
| Comparative example 3 | 0.979 | 1.007 | 1.029 | 0.943 | 0.886 | 0.940 | 0.598 | 0.400 | 0.669 |

TABLE 3

|  | Water permeability (pure water) | | | Water permeability (inulin) | | | Water permeability (dextran T10) | | | Water permeability (dextran T40) | | |
|---|---|---|---|---|---|---|---|---|---|---|---|---|
|  | Before contact with medium | After contact with medium | Change ratio | Before contact with medium | After contact with medium | Change ratio | Before contact with medium | After contact with medium | Change ratio | Before contact with medium | After contact with medium | Change ratio |
| Example 1 | 167 | 69 | 0.413 | 155 | 57 | 0.368 | 135 | 52 | 0.385 | 76 | 45 | 0.592 |
| Example 2 | 175 | 70 | 0.400 | 157 | 54 | 0.344 | 137 | 55 | 0.401 | 73 | 44 | 0.603 |
| Example 3 | 198 | 122 | 0.616 | 175 | 85 | 0.486 | 148 | 91 | 0.615 | 102 | 67 | 0.657 |
| Comparative example 1 | 235 | 175 | 0.745 | 228 | 164 | 0.719 | 202 | 158 | 0.782 | 158 | 124 | 0.785 |
| Comparative example 2 | 271 | 183 | 0.675 | 225 | 184 | 0.818 | 225 | 178 | 0.791 | 162 | 145 | 0.895 |
| Comparative example 3 | 258 | 230 | 0.891 | 223 | 230 | 1.031 | 238 | 216 | 0.908 | 916 | 168 | 0.857 |

(Cell Culture Experiment 1 Using Hollow-Fiber Module: Use of General Medium)

FIG. 2 shows a configuration of a culture apparatus used in the cell culture experiment in a simplified manner. For the cell culture experiment, the modules described in Examples 1 to 3 of the present invention and in Comparative Examples 1 to 3 in the present invention were used. Primary human mesenchymal stem cells purchased from Takara Bio Inc. were used as cells. The cell seeding density was 1900 cells/cm$^2$. The flow rate of the medium was 0.33 mm/min in the inner cavity of the hollow-fiber membrane and 3.46 mm/min in the outer cavity of the hollow-fiber membrane. In addition, Culture Bag 1 L (manufactured by Nipro Corporation) (5 and 6 in FIG. 2) was used for supplying the medium. DMEM containing fetal bovine serum in an amount of 10 vol % was used as the medium. As medium perfusion pumps, total two Perista Biominipumps (manufactured by ATTO Corporation) (30 and 31 in FIG. 2) were used for perfusion on the inner cavity side and for perfusion on the outer cavity side in the hollow-fiber membrane were used. Cells were cultured in a $CO_2$ incubator at 37° C. for 7 days. As a method for supplying the medium, the medium was supplied in one direction on both the inner cavity side in the hollow-fiber membrane and the outer cavity side in the hollow-fiber membrane. Mesenchymal stem cells were seeded on the inner cavity side in the hollow-fiber membrane, and left standing for 2 days, and perfusion on the inner cavity side in the hollow-fiber membrane was then started. After the cells were cultured for 7 days, perfusion of the medium was stopped, and the cells grown in the hollow-fiber module were collected. During collection of the cells, a 0.25% trypsin solution (manufactured by Life Technologies, Inc.) as a cell dissociation reagent was used.

(Cell Culture Experiment 2 Using Hollow-Fiber Module: Use of Low-Serum Medium)

Cell culture experiment 2 was conducted using the same cell culture apparatus as in cell culture experiment 1 The hollow-fiber modules described in Examples 1 to 3 of the present invention and in Comparative Examples 1 to 3 were used, and primary human mesenchymal stem cells purchased from Takara Bio Inc. were used as cells. In this experiment, MF-medium (registered trademark) Mesenchymal Stem Cell Growing Medium (manufactured by TOYOBO CO., LTD.) containing fetal bovine serum in an amount of 1 vol % was used as a medium. For other conditions, the experiment was conducted in the same manner as in cell culture experiment 1.

(Cell Culture Experiment 3 Using Hollow-Fiber Module Use of Serum-Free Medium)

Cell culture experiment 3 was conducted using the same cell culture apparatus as in cell culture experiment 1. The hollow-fiber modules described in Examples 1 to 3 of the present invention and in Comparative Examples 1 to 3 were used, and primary human mesenchymal stem cells purchased from Takara Bio Inc. were used as cells. In this experiment, serum-free MF-medium (registered trademark) Mesenchymal Stem Cell Growing Medium (manufactured by TOYOBO CO., LTD.) was used as a medium. For other conditions, the experiment was conducted in the same manner as in cell culture experiment 1.

The results of cell culture experiments 1 to 3 are collectively shown in Table 4.

In the cell culture experiment 1, use of the hollow-fiber membranes (hollow-fiber modules) of Examples 1 to 3 which contained a hydrophobic polymer and a hydrophilic polymer according to the present invention made it possible to obtain a favorable cell growth rate in culture using a general medium: DMEM containing fetal bovine serum in an amount of 10 vol %. On the other hand, when the hollow-fiber membranes (hollow-fiber modules) of Comparative Examples 1 to 3 were used, growth of cells hardly occurred.

In cell culture experiment 2, a culture experiment was conducted using a mesenchymal stem cell-dedicated medium that was specific to culture of mesenchymal stem cells, and had a low serum concentration (1 vol %). In this culture experiment, the hollow-fiber membranes (hollow-fiber modules) of Examples 1 to 3 which contained a hydrophobic polymer and a hydrophilic polymer according to the present invention exhibited a favorable cell growth rate.

Further, in cell culture experiment 3, a culture experiment was conducted using a serum-free medium, which did not contain serum, as the mesenchymal stem cell-dedicated medium. In this cell culture experiment, the hollow-fiber membranes (hollow-fiber modules) of Examples 1 to 3 which contained a hydrophobic polymer and a hydrophilic polymer according to the present invention exhibited a favorable cell growth rate.

On the other hand, when the hollow-fiber membranes (hollow-fiber modules) of comparative examples were used, growth of cells hardly occurred.

That is, hollow-fiber membranes excellent as a cell culture substrate may be those in which the content of the hydrophilic polymer in the whole membrane is more than 0% by mass and less than 1% by mass, and the content of the hydrophilic polymer on a membrane surface is more than 0% by mass and less than 10% by mass.

(Measurement of Cell Growth Rate)

The cell growth rate was calculated from the following equation using the number of living cells collected from the cell culture container (hollow-fiber module) after completion of culture and the initial number of seeded cells. The number of cells was measured in accordance with a method as described later.

cell growth rate (%)=(number of collected living cells−number of seeded cells)/number of seeded cells×100

(Measurement of Number of Cells)

A collected liquid containing cells was finally suspended in 1 ml of a culture liquid by a centrifugal separation operation. A liquid obtained by mixing the resulting suspension liquid and a trypan blue stain liquid at a ratio of 1:1 was added to a hemocytometer, and the number of cells was measured under a microscope.

1. Surfaces of a hemocytometer and a cover glass are washed with 70% isopropanol, wiped to remove excess isopropanol, and air-dried.

2. A side surface of the cover glass is wetted with reagent grade water, and bonded to the hemocytometer.

3. A cell suspension liquid is thoroughly stirred by a Pasteur pipette or the like, and then immediately poured into the hemocytometer up to above the slit.
4. The above-described operations 1 to 3 are carried out using another hemocytometer (measurement is performed twice, and the measurements are averaged).
5. The hemocytometer is placed on a microscope, and a focus is put on the grid line (objective lens at a magnification of 10 times).
6. The number of cells in an area of 1 mm² is quickly measured using a counter.
* In consideration of a high possibility of occurrence of errors, at least 100 to 500 cells should be measured for correct counting.

Calculation Method:

$$C = N \times 10^4$$

C: number of cells per ml
N: average of numbers of measured cells
$10^4$: converted value of volume for 1 mm²
Total number = C×V
V = volume of liquid in which cells are suspended

TABLE 4

| | Cell growth rate (ratio) | | |
|---|---|---|---|
| | Medium containing 10% of serum | Medium containing 1% of serum | Serum-free medium |
| Example 1 | 11.8 | 14.8 | 6.2 |
| Example 2 | 10.4 | 13.2 | 5.3 |

TABLE 4-continued

| | Cell growth rate (ratio) | | |
|---|---|---|---|
| | Medium containing 10% of serum | Medium containing 1% of serum | Serum-free medium |
| Example 3 | 9.8 | 12.9 | 4.7 |
| Comparative Example 1 | 3.1 | 3.3 | 2.4 |
| Comparative example 1 | 2.7 | 3.1 | 2.0 |
| Comparative example 3 | 2.4 | 2.8 | 1.9 |

(Measurement of Cell Surface Marker)

Surface marker measurement was performed before culture and after culture for 7 days for confirming that the performance of mesenchymal stem cells was maintained even after culture. On the basis of the statement of ISCT (International Society for Cellular Therapy), the surface marker measurement was based on the premise that CD105, CD73 and CD90 are positive (≥95%), and CD45, CD34, CD11b, CD19 and HLA-DR are negative (≤2%).

Measurement of surface marker expression was performed using a flow cytometer (BD FACSCalibur manufactured by BD Company). Human MSC Analysis Kit (manufactured by BD Company) was used as an antibody.

The results of performing surface marker measurement of mesenchymal stem cells before and after culture are shown in Table 5 (before culture) and Table 6 (after culture). Since the expression pattern of the cell surface marker was not changed before and after culture using the hollow-fiber module, it was confirmed that the properties of mesenchymal stem cells were maintained.

TABLE 5

| | CD105 | CD73 | CD90 | CD45 | CD34 | CD11b | CD19 | HLA-DR |
|---|---|---|---|---|---|---|---|---|
| Example 1 | + | + | + | − | − | − | − | − |
| Example 2 | + | + | + | − | − | − | − | − |
| Example 3 | + | + | + | − | − | − | − | − |
| Comparative example 1 | + | + | + | − | − | − | − | − |
| Comparative example 2 | + | + | + | − | − | − | − | − |
| Comparative example 3 | + | + | + | − | − | − | − | − |

+: positive (≥93%),
−: negative (≤2%)

TABLE 6

| | CD105 | CD73 | CD90 | CD45 | CD34 | CD11b | CD19 | HLA-DR |
|---|---|---|---|---|---|---|---|---|
| Example 1 | + | + | + | − | − | − | − | − |
| Example 2 | + | + | + | − | − | − | − | − |
| Example 3 | + | + | + | − | − | − | − | − |
| Comparative example 1 | + | + | + | − | − | − | − | − |
| Comparative example 2 | + | + | + | − | − | − | − | − |
| Comparative example 3 | + | + | + | − | − | − | − | − |

+: positive (≥95%),
−: negative (≤2%)

INDUSTRIAL APPLICABILITY

According to the present invention, it is possible to provide a hollow-fiber membrane as a culture substrate which does not require a coating treatment with a cell adhesion factor. In addition, when the hollow-fiber membrane of the present invention is used, it is possible to construct and provide a cell culture system capable of easily and efficiently culturing various kinds of cells such as mesenchymal stem cells.

REFERENCE SIGNS LIST

- 1a, 1b: End conduit
- 2a, 2b: Side conduit
- 3: Module case
- 4: Culture substrate (hollow-fiber membrane)
- 5, 6: Liquid medium storage container
- 7: Waste liquid collection solution or cell collection container
- 21, 22, 23, 24, 25, 26, 27, 28: Valve
- 41, 42, 43: Sterile connector
- 8: Cell culture container (hollow-fiber module)
- 30, 31: Pump
- 50: $CO_2$ incubator
- 60: Operation controller (operation panel)

The invention claimed is:

1. A hollow-fiber membrane for cell culture which is to be used as a culture substrate for adhesive cells, comprising:
   a hydrophobic polymer, and
   a hydrophilic polymer,
   wherein a content of the hydrophilic polymer in a whole hollow-fiber membrane is more than 0% by mass and less than 1% by mass,
   wherein a content of the hydrophilic polymer on an inner surface of the hollow-fiber membrane is more than 0% by mass and less than 10% by mass, and
   wherein the content of the hydrophilic polymer on the inner surface of the hollow-fiber membrane is greater than the content of the hydrophilic polymer in the whole hollow-fiber membrane.

2. The hollow-fiber membrane according to claim 1, wherein the hydrophobic polymer is at least one selected from the group consisting of polyether sulfone, polysulfone, polyvinylidene fluoride and polyethylene.

3. The hollow-fiber membrane according to claim 1, wherein the hydrophilic polymer is at least one selected from the group consisting of polyvinyl pyrrolidone, polyethylene glycol, polyvinyl alcohol, carboxymethyl cellulose and starch.

4. A hollow-fiber module for cell culture which contains a hollow fiber bundle obtained by bundling more than one hollow-fiber membrane according to claim 1.

5. A method for culturing cells using the hollow-fiber module according to claim 4 as a cell culture container.

6. A cell culture apparatus including the hollow-fiber module according to claim 4 as a cell culture container.

7. The hollow-fiber membrane according to claim 1, wherein the content of the hydrophilic polymer on the inner surface of the hollow-fiber membrane is greater than or equal to 4.3% by mass and less than 10% by mass.

* * * * *